US011925493B2

(12) United States Patent
Haley et al.

(10) Patent No.: US 11,925,493 B2
(45) Date of Patent: *Mar. 12, 2024

(54) VISUALIZATION, NAVIGATION, AND PLANNING WITH ELECTROMAGNETIC NAVIGATION BRONCHOSCOPY AND CONE BEAM COMPUTED TOMOGRAPHY INTEGRATED

(71) Applicant: Covidien LP, Mansfield, MA (US)

(72) Inventors: Kaylen J. Haley, Longmont, CO (US); William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 189 days.

This patent is subject to a terminal disclaimer.

(21) Appl. No.: 17/516,810

(22) Filed: Nov. 2, 2021

(65) Prior Publication Data
US 2022/0054097 A1 Feb. 24, 2022

Related U.S. Application Data

(63) Continuation of application No. 15/370,906, filed on Dec. 6, 2016, now Pat. No. 11,172,895.
(Continued)

(51) Int. Cl.
*A61B 6/12* (2006.01)
*A61B 1/267* (2006.01)
(Continued)

(52) U.S. Cl.
CPC .............. *A61B 6/12* (2013.01); *A61B 5/062* (2013.01); *A61B 6/032* (2013.01); *A61B 6/4085* (2013.01);
(Continued)

(58) Field of Classification Search
CPC ......... A61B 6/12; A61B 6/032; A61B 6/4085; A61B 6/463; A61B 6/487; A61B 6/4441;
(Continued)

(56) References Cited

U.S. PATENT DOCUMENTS

| 4,587,975 A | 5/1986 | Salo et al. |
| 4,593,687 A | 6/1986 | Gray |

(Continued)

FOREIGN PATENT DOCUMENTS

| CA | 2655001 A1 | 8/2010 |
| CA | 2923457 A1 | 3/2015 |

(Continued)

OTHER PUBLICATIONS

Leira et al., A novel research platform for electromagnetic navigated bronchoscopy using cone beam CT imaging and an animal model. Minim Invasive Ther Allied Technol. Jan. 2011;20(1):30-41. doi: 10.3109/13645706.2010.518747. Epub Sep. 27, 2010 (Year: 2011).*

(Continued)

*Primary Examiner* — John D Li
(74) *Attorney, Agent, or Firm* — Weber Rosselli & Cannon LLP

(57) ABSTRACT

The present disclosure relates to systems, devices and methods for providing visual guidance for navigating inside a patient's chest. An exemplary method includes presenting a three-dimensional (3D) model of a luminal network, generating, by an electromagnetic (EM) field generator, an EM field about the patient's chest, detecting a location of an EM sensor within the EM field, determining a position of a tool within the patient's chest based on the detected location of the EM sensor, displaying an indication of the position of the tool on the 3D model, receiving cone beam computed tomography (CBCT) image data of the patient's chest, detecting the location of the tool within the patient's chest (Continued)

based on the CBCT image data, and updating the indication of the position of the tool on the 3D model based on the detected location.

20 Claims, 9 Drawing Sheets

Related U.S. Application Data

(60) Provisional application No. 62/264,145, filed on Dec. 7, 2015.

(51) Int. Cl.
| | |
|---|---|
| *A61B 5/06* | (2006.01) |
| *A61B 6/00* | (2006.01) |
| *A61B 6/03* | (2006.01) |
| *A61B 10/02* | (2006.01) |
| *A61B 18/00* | (2006.01) |
| *A61B 18/12* | (2006.01) |
| *A61B 18/14* | (2006.01) |
| *A61B 18/18* | (2006.01) |
| *A61B 34/20* | (2016.01) |
| *A61B 90/00* | (2016.01) |
| *G16H 50/50* | (2018.01) |

(52) U.S. Cl.
CPC .............. *A61B 6/463* (2013.01); *A61B 6/487* (2013.01); *A61B 10/02* (2013.01); *A61B 18/1206* (2013.01); *A61B 18/1492* (2013.01); *A61B 18/1815* (2013.01); *A61B 34/20* (2016.02); *A61B 90/37* (2016.02); *G16H 50/50* (2018.01); *A61B 1/267* (2013.01); *A61B 6/4441* (2013.01); *A61B 6/466* (2013.01); *A61B 2018/00541* (2013.01); *A61B 2018/00577* (2013.01); *A61B 2018/00982* (2013.01); *A61B 2018/1823* (2013.01); *A61B 2034/2051* (2016.02); *A61B 2090/3764* (2016.02)

(58) Field of Classification Search
CPC ......... A61B 6/446; A61B 34/20; A61B 90/37; A61B 5/062; A61B 18/1206; A61B 18/1492; A61B 18/1815; A61B 2034/2051; A61B 2090/3764; A61B 1/267; A61B 2018/00541; A61B 2018/00577; A61B 2018/00982; A61B 2018/1823; G16H 50/50
See application file for complete search history.

(56) References Cited

U.S. PATENT DOCUMENTS

| | | | |
|---|---|---|---|
| 5,419,324 | A | 5/1995 | Dillow |
| 5,797,849 | A | 8/1998 | Vesely et al. |
| 5,852,646 | A | 12/1998 | Klotz et al. |
| 5,930,329 | A | 7/1999 | Navab |
| 5,951,475 | A | 9/1999 | Gueziec et al. |
| 5,963,612 | A | 10/1999 | Navab |
| 5,963,613 | A | 10/1999 | Navab |
| 6,028,912 | A | 2/2000 | Navab |
| 6,038,282 | A | 3/2000 | Wiesent et al. |
| 6,049,582 | A | 4/2000 | Navab |
| 6,050,724 | A | 4/2000 | Schmitz et al. |
| 6,055,449 | A | 4/2000 | Navab |
| 6,081,577 | A | 6/2000 | Webber |
| 6,120,180 | A | 9/2000 | Graumann |
| 6,167,296 | A | 12/2000 | Shahidi |
| 6,188,355 | B1 | 2/2001 | Gilboa |
| 6,236,704 | B1 | 5/2001 | Navab et al. |
| 6,314,310 | B1 | 11/2001 | Ben-Haim et al. |
| 6,317,621 | B1 | 11/2001 | Graumann et al. |
| 6,351,513 | B1 | 2/2002 | Bani-Hashemi et al. |
| 6,351,573 | B1 | 2/2002 | Schneider |
| 6,381,483 | B1 | 4/2002 | Hareyama et al. |
| 6,389,104 | B1 | 5/2002 | Bani-Hashemi et al. |
| 6,404,843 | B1 | 6/2002 | Vaillant |
| 6,424,731 | B1 | 7/2002 | Launay et al. |
| 6,470,207 | B1 | 10/2002 | Simon et al. |
| 6,484,049 | B1 | 11/2002 | Seeley et al. |
| 6,485,422 | B1 | 11/2002 | Mikus et al. |
| 6,490,475 | B1 | 12/2002 | Seeley et al. |
| 6,491,430 | B1 | 12/2002 | Seissler |
| 6,520,934 | B1 | 2/2003 | Lee et al. |
| 6,535,756 | B1 | 3/2003 | Simon et al. |
| 6,539,127 | B1 | 3/2003 | Roche et al. |
| 6,546,068 | B1 | 4/2003 | Shimura |
| 6,546,279 | B1 | 4/2003 | Bova et al. |
| 6,549,607 | B1 | 4/2003 | Webber |
| 6,628,977 | B2 | 9/2003 | Graumann et al. |
| 6,697,664 | B2 | 2/2004 | Kienzle, III et al. |
| 6,707,878 | B2 | 3/2004 | Claus et al. |
| 6,714,810 | B2 | 3/2004 | Grzeszczuk et al. |
| 6,725,080 | B2 | 4/2004 | Melkent et al. |
| 6,731,283 | B1 | 5/2004 | Navab |
| 6,731,970 | B2 | 5/2004 | Schlossbauer et al. |
| 6,768,784 | B1 | 7/2004 | Green et al. |
| 6,782,287 | B2 | 8/2004 | Grzeszczuk et al. |
| 6,785,356 | B2 | 8/2004 | Grass et al. |
| 6,785,571 | B2 | 8/2004 | Glossop |
| 6,801,597 | B2 | 10/2004 | Webber |
| 6,823,207 | B1 | 11/2004 | Jensen et al. |
| 6,856,826 | B2 | 2/2005 | Seeley et al. |
| 6,856,827 | B2 | 2/2005 | Seeley et al. |
| 6,865,253 | B2 | 3/2005 | Blumhofer et al. |
| 6,898,263 | B2 | 5/2005 | Avinash et al. |
| 6,944,260 | B2 | 9/2005 | Hsieh et al. |
| 6,956,927 | B2 | 10/2005 | Sukeyasu et al. |
| 7,010,080 | B2 | 3/2006 | Mitschke et al. |
| 7,010,152 | B2 | 3/2006 | Bojer et al. |
| 7,033,325 | B1 | 4/2006 | Sullivan |
| 7,035,371 | B2 | 4/2006 | Boese et al. |
| 7,106,825 | B2 | 9/2006 | Gregerson et al. |
| 7,117,027 | B2 | 10/2006 | Zheng et al. |
| 7,129,946 | B2 | 10/2006 | Ditt et al. |
| 7,130,676 | B2 | 10/2006 | Barrick |
| 7,165,362 | B2 | 1/2007 | Jobs et al. |
| 7,251,522 | B2 | 7/2007 | Essenreiter et al. |
| 7,321,677 | B2 | 1/2008 | Evron et al. |
| 7,327,872 | B2 | 2/2008 | Vaillant et al. |
| 7,343,195 | B2 | 3/2008 | Strommer et al. |
| 7,356,367 | B2 | 4/2008 | Liang et al. |
| 7,369,641 | B2 | 5/2008 | Tsubaki et al. |
| 7,440,538 | B2 | 10/2008 | Tsujii |
| 7,467,007 | B2 | 12/2008 | Lothert |
| 7,474,913 | B2 | 1/2009 | Durlak |
| 7,499,743 | B2 | 3/2009 | Vass et al. |
| 7,502,503 | B2 | 3/2009 | Bojer et al. |
| 7,505,549 | B2 | 3/2009 | Ohishi et al. |
| 7,505,809 | B2 | 3/2009 | Strommer et al. |
| 7,508,388 | B2 | 3/2009 | Barfuss et al. |
| 7,587,074 | B2 | 9/2009 | Zarkh et al. |
| 7,603,155 | B2 | 10/2009 | Jensen |
| 7,620,223 | B2 | 11/2009 | Xu et al. |
| 7,639,866 | B2 | 12/2009 | Pomero et al. |
| 7,664,542 | B2 | 2/2010 | Boese et al. |
| 7,689,019 | B2 | 3/2010 | Boese et al. |
| 7,689,042 | B2 | 3/2010 | Brunner et al. |
| 7,693,263 | B2 | 4/2010 | Bouvier et al. |
| 7,697,972 | B2 | 4/2010 | Verard et al. |
| 7,711,082 | B2 | 5/2010 | Fujimoto et al. |
| 7,711,083 | B2 | 5/2010 | Heigl et al. |
| 7,711,409 | B2 | 5/2010 | Keppel et al. |
| 7,720,520 | B2 | 5/2010 | Willis |
| 7,725,165 | B2 | 5/2010 | Chen et al. |
| 7,734,329 | B2 | 6/2010 | Boese et al. |
| 7,742,557 | B2 | 6/2010 | Brunner et al. |
| 7,742,629 | B2 | 6/2010 | Zarkh et al. |
| 7,761,135 | B2 | 7/2010 | Pfister et al. |

(56) References Cited

U.S. PATENT DOCUMENTS

| | | |
|---|---|---|
| 7,778,685 B2 | 8/2010 | Evron et al. |
| 7,787,932 B2 | 8/2010 | Vilsmeier et al. |
| 7,804,991 B2 | 9/2010 | Abovitz et al. |
| 7,831,096 B2 | 11/2010 | Williamson, Jr. |
| 7,835,779 B2 | 11/2010 | Anderson et al. |
| 7,853,061 B2 | 12/2010 | Gorges et al. |
| 7,877,132 B2 | 1/2011 | Rongen et al. |
| 7,899,226 B2 | 3/2011 | Pescatore et al. |
| 7,907,989 B2 | 3/2011 | Borgert et al. |
| 7,912,180 B2 | 3/2011 | Zou et al. |
| 7,912,262 B2 | 3/2011 | Timmer et al. |
| 7,941,000 B2 | 5/2011 | Rongen et al. |
| 7,949,088 B2 | 5/2011 | Nishide et al. |
| 7,991,450 B2 | 8/2011 | Virtue et al. |
| 7,995,819 B2 | 8/2011 | Vaillant et al. |
| 8,000,436 B2 | 8/2011 | Seppi et al. |
| 8,043,003 B2 | 10/2011 | Vogt et al. |
| 8,045,780 B2 | 10/2011 | Boese et al. |
| 8,050,739 B2 | 11/2011 | Eck et al. |
| 8,090,168 B2 | 1/2012 | Washburn et al. |
| 8,098,914 B2 | 1/2012 | Liao et al. |
| 8,111,894 B2 | 2/2012 | Van De Haar |
| 8,111,895 B2 | 2/2012 | Spahn |
| 8,126,111 B2 | 2/2012 | Uhde et al. |
| 8,126,241 B2 | 2/2012 | Zarkh et al. |
| 8,150,131 B2 | 4/2012 | Harer et al. |
| 8,180,132 B2 | 5/2012 | Gorges et al. |
| 8,195,271 B2 | 6/2012 | Rahn |
| 8,200,316 B2 | 6/2012 | Keppel et al. |
| 8,208,708 B2 | 6/2012 | Homan et al. |
| 8,218,843 B2 | 7/2012 | Edlauer et al. |
| 8,229,061 B2 | 7/2012 | Hanke et al. |
| 8,238,625 B2 | 8/2012 | Strommer et al. |
| 8,248,413 B2 | 8/2012 | Gattani et al. |
| 8,270,691 B2 | 9/2012 | Xu et al. |
| 8,271,068 B2 | 9/2012 | Khamene et al. |
| 8,275,448 B2 | 9/2012 | Camus et al. |
| 8,295,577 B2 | 10/2012 | Zarkh et al. |
| 8,306,303 B2 | 11/2012 | Bruder et al. |
| 8,311,617 B2 | 11/2012 | Keppel et al. |
| 8,320,992 B2 | 11/2012 | Frenkel et al. |
| 8,340,379 B2 | 12/2012 | Razzaque et al. |
| 8,345,817 B2 | 1/2013 | Fuchs et al. |
| 8,346,344 B2 | 1/2013 | Pfister et al. |
| 8,358,874 B2 | 1/2013 | Haras |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,504,588 B2 | 8/2013 | Hirschbeck et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,865 B2 | 1/2014 | Zarkh et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,044,254 B2 | 6/2015 | Ladtkow et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,247,992 B2 | 2/2016 | Ladtkow et al. |
| 9,247,993 B2 | 2/2016 | Ladtkow et al. |
| 9,259,269 B2 | 2/2016 | Ladtkow et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,370,398 B2 | 6/2016 | Ladtkow et al. |
| 9,401,047 B2 | 7/2016 | Bogoni et al. |
| 9,406,134 B2 | 8/2016 | Klingenbeck-Regn |
| 9,445,772 B2 | 9/2016 | Callaghan |
| 9,445,776 B2 | 9/2016 | Han et al. |
| 9,466,135 B2 | 10/2016 | Koehler et al. |
| 11,172,895 B2 | 11/2021 | Dickhans et al. |
| 2002/0143324 A1 | 10/2002 | Edwards |
| 2003/0220555 A1 | 11/2003 | Heigl et al. |
| 2004/0143317 A1 | 7/2004 | Stinson et al. |
| 2005/0008210 A1 | 1/2005 | Evron et al. |
| 2005/0027193 A1 | 2/2005 | Mitschke et al. |
| 2005/0215874 A1 | 9/2005 | Wang et al. |
| 2006/0002630 A1 | 1/2006 | Fu et al. |
| 2006/0023840 A1 | 2/2006 | Boese |
| 2007/0049861 A1 | 3/2007 | Gundel |
| 2007/0232898 A1 | 10/2007 | Huynh et al. |
| 2008/0033420 A1 | 2/2008 | Nields et al. |
| 2008/0119725 A1 | 5/2008 | Lloyd |
| 2008/0178880 A1 | 7/2008 | Christopher |
| 2008/0243142 A1 | 10/2008 | Gildenberg |
| 2008/0262346 A1 | 10/2008 | Assis et al. |
| 2009/0080737 A1 | 3/2009 | Battle et al. |
| 2009/0216112 A1 | 8/2009 | Assis et al. |
| 2009/0281417 A1 | 11/2009 | Hartmann et al. |
| 2009/0287443 A1 | 11/2009 | Jascob et al. |
| 2011/0085720 A1 | 4/2011 | Averbuch |
| 2011/0112398 A1 | 5/2011 | Zarkh et al. |
| 2012/0109260 A1* | 5/2012 | Stancer .............. A61N 1/39622 607/60 |
| 2012/0281903 A1 | 11/2012 | Trumer et al. |
| 2013/0116739 A1 | 5/2013 | Brada et al. |
| 2013/0259338 A1 | 10/2013 | Brehm |
| 2013/0259341 A1 | 10/2013 | Mountney et al. |
| 2013/0279780 A1 | 10/2013 | Grbic et al. |
| 2014/0046211 A1 | 2/2014 | Ladtkow et al. |
| 2014/0148808 A1* | 5/2014 | Inkpen .................. A61B 90/06 73/866.5 |
| 2014/0270441 A1 | 9/2014 | Baker |
| 2014/0281961 A1 | 9/2014 | Baker |
| 2014/0282216 A1 | 9/2014 | Baker |
| 2014/0343416 A1 | 11/2014 | Panescu et al. |
| 2015/0042643 A1 | 2/2015 | Shibata et al. |
| 2015/0088120 A1 | 3/2015 | Garcia |
| 2015/0227679 A1 | 8/2015 | Kamer et al. |
| 2016/0000302 A1 | 1/2016 | Brown et al. |
| 2016/0000356 A1 | 1/2016 | Brown et al. |
| 2016/0005168 A1 | 1/2016 | Merlet |
| 2016/0005194 A1 | 1/2016 | Schretter et al. |
| 2016/0120521 A1 | 5/2016 | Weingarten et al. |
| 2016/0166329 A1 | 6/2016 | Langan |
| 2016/0206380 A1 | 7/2016 | Sparks et al. |

(56) References Cited

U.S. PATENT DOCUMENTS

2016/0287343 A1 10/2016 Eichler et al.
2017/0340240 A1 11/2017 Jacobsen

FOREIGN PATENT DOCUMENTS

| CN | 103402453 A | 11/2013 |
|---|---|---|
| CN | 104582622 A | 4/2015 |
| DE | 10323008 A1 | 12/2004 |
| WO | 2007113703 A2 | 10/2007 |
| WO | 2012177470 A1 | 12/2012 |
| WO | 2015087206 A1 | 6/2015 |
| WO | 2015089013 A1 | 6/2015 |

OTHER PUBLICATIONS

Yaniv Ziv et al., "Electromagnetic tracking in the clinical environment", Medical Physics, vol. 36, No. 3, Mar. 2009, pp. 876-892.

Extended European Search Report issued by the European Patent Office, corresponding to European Patent Application No. 16202781.7; dated Apr. 24, 2017 (8 pages).
European Examination Report for application No. 16 202 781.7 dated Mar. 9, 2018, 3 pages.
Chinese Office Action issued in Appl. No. CN 201611117979.6 dated Oct. 9, 2018, together with English language translation (15 pages).
Chinese Office Action issue in correspdong Appl. No. CN 201611117979.6 dated May 21, 2019, together with English language translation (7 pages).
Leira et al., A novel research platform for electromagnetic navigated bronchoscopy using cone beam CT imaging and an animal model. Minim Invasive TherAllied Technol. Jan. 2011;20(1):30-41. doi: 10.3109/13645706.2010.518747. Epub Sep. 27, 2010. (Year: 2010).
Lugez et al, Electromagnetic tracking in surgical and interventional environments: usability study, International Journal of Computer Assisted Radiology and Surge5b4ry, Mar. 2015, vol. 10, Issue 3, pp. 253-262. Epub Sep. 6, 2014. (Year: 2014).

\* cited by examiner

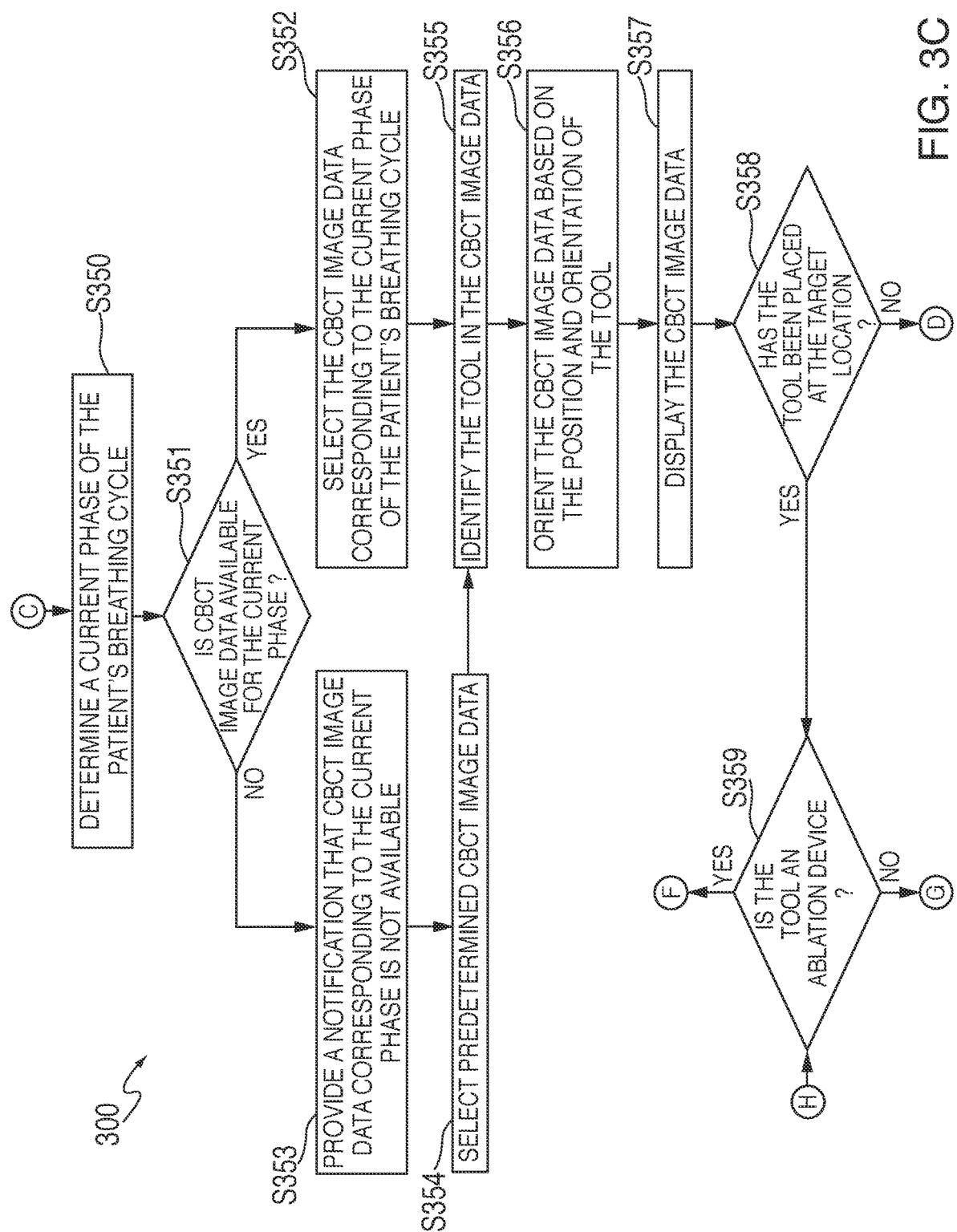

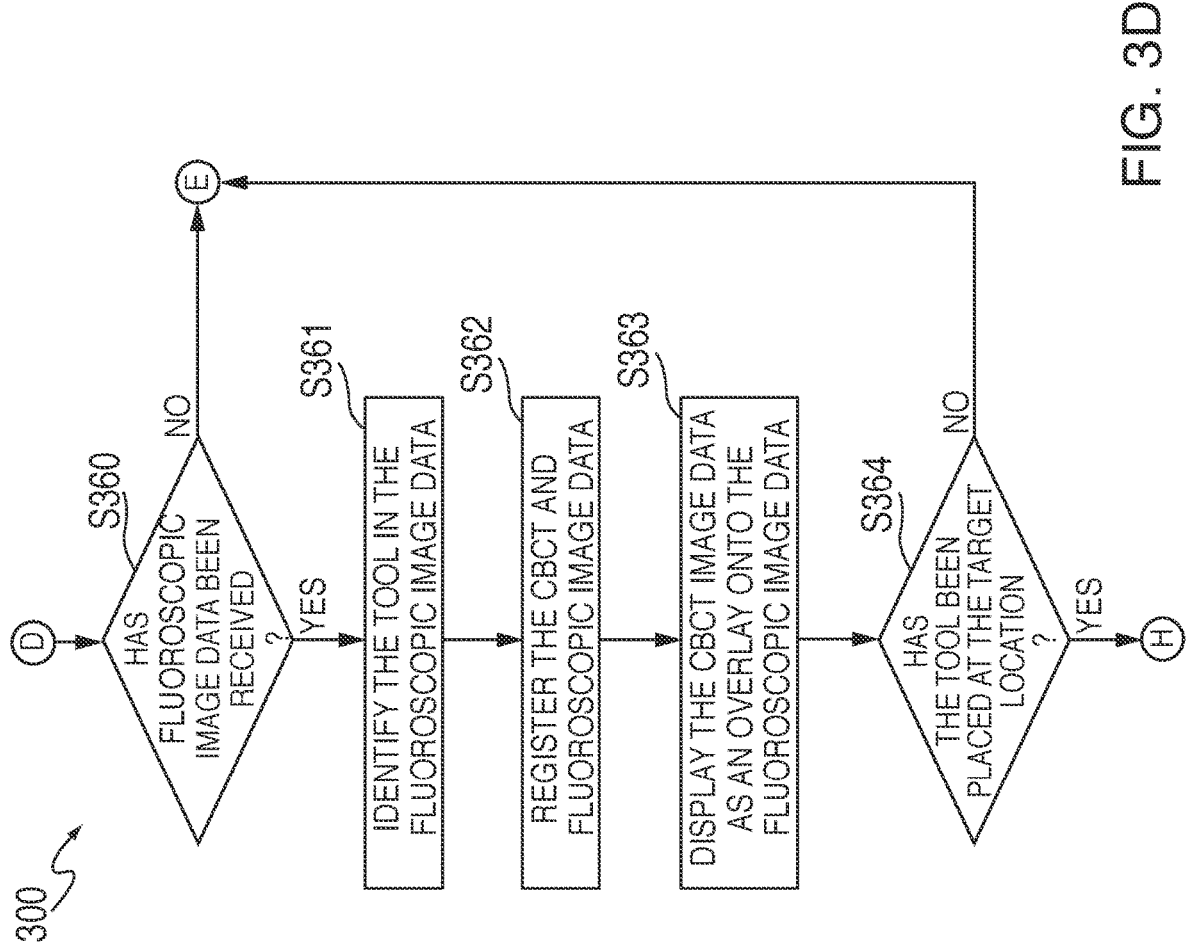

VISUALIZATION, NAVIGATION, AND PLANNING WITH ELECTROMAGNETIC NAVIGATION BRONCHOSCOPY AND CONE BEAM COMPUTED TOMOGRAPHY INTEGRATED

CROSS-REFERENCE TO RELATED APPLICATIONS

The present application is a continuation of U.S. patent application Ser. No. 15/370,906, filed on Dec. 6, 2016, which claims the benefit of and priority to U.S. Provisional Patent Application Ser. No. 62/264,145 entitled VISUALIZATION, NAVIGATION, AND PLANNING WITH ELECTROMAGNETIC NAVIGATION BRONCHOSCOPY AND CONE BEAM COMPUTED TOMOGRAPHY INTEGRATED, filed on Dec. 7, 2015, by Haley et al., the entire contents of each of which being incorporated by reference herein.

BACKGROUND

Technical Field

The present disclosure relates to tools for assisting surgeons during performance of medical procedures, and more particularly, to systems, devices, and methods for providing image-based guidance during medical procedures.

Description of Related Art

Pulmonary disease may cause one or more portions of a patient's lungs may lose its ability to function normally and thus may need to be treated. Lung treatment procedures may be very complex and would be greatly aided if the surgeon performing the procedure can visualize the way airways and other structures in the patient's lungs are shaped and where tools are located. Traditional pre-operative images are helpful, to an extent, with the former, but provide no guidance with regard to the latter.

Systems for displaying images and tracking tools in the patient's lungs generally rely on pre-operative data, such as from computed tomography (CT) scans performed before, sometimes days or weeks in advance, the treatment procedure begins. However, such systems do not account for changes that may have occurred after the CT scan was performed, or for movement occurring during the treatment procedure. Systems, devices, and methods for improving on the process of identifying and visualizing a patient's lungs, as well as structures and tools located therein, are described below.

SUMMARY

Provided in accordance with the present disclosure is a method of providing visual guidance for navigating inside a patient's chest. According to an embodiment of the present disclosure, the method includes presenting a three-dimensional (3D) model of a luminal network, generating, by an electromagnetic (EM) field generator, an EM field about the patient's chest, detecting a location of an EM sensor within the EM field, determining a position of a tool within the patient's chest based on the detected location of the EM sensor, displaying an indication of the position of the tool on the 3D model, receiving cone beam computed tomography (CBCT) image data of the patient's chest, detecting the location of the tool within the patient's chest based on the CBCT image data, and updating the indication of the position of the tool on the 3D model based on the detected location.

In another aspect of the present disclosure, the method further includes providing guidance for positioning a CBCT imaging device based on the detected location of the EM sensor.

In yet another aspect of the present disclosure, the method further includes imaging a portion of the patient's chest about the detected location of the EM sensor to generate the CBCT image data.

In a further aspect of the present disclosure, the presented 3D model includes an indication of a target location and a pathway for navigating the tool to the target location.

In yet a further aspect of the present disclosure, a first portion of the pathway to the target location is located inside of the luminal network and a second portion of the pathway to the target location is located outside of the luminal network.

In still a further aspect of the present disclosure, the CBCT data is received while the tool is navigated along the second portion of the pathway to the target location.

In yet a further aspect of the present disclosure, the second portion of the pathway to the target location is updated based on the CBCT data.

In another aspect of the present disclosure, the method further includes providing a notification that the EM field may be distorted based on the position of the CBCT imaging device.

In a further aspect of the present disclosure, the EM field generator compensates for distortion of the EM field based on the position of the CBCT imaging device.

In another aspect of the present disclosure, the method further includes providing a notification when one or more EM sensors on the patient's chest indicate that the patient has moved during the imaging.

In yet another aspect of the present disclosure, the method further includes disabling the EM field generator prior to imaging the portion of the patient's chest, and enabling the EM field generator after imaging the portion of the patient's chest.

In still another aspect of the present disclosure, the CBCT image data is generated during a first phase of the patient's respiratory cycle, and the method further includes imaging the portion of the patient's chest about the detected location of the EM sensor to generate additional CBCT image data during a second phase of the patient's respiratory cycle.

In a further aspect of the present disclosure, the method further includes monitoring the patient's respiratory cycle to determine a current phase of the patient's respiratory cycle, and displaying one of the CBCT image data or the additional CBCT image data corresponding to the current phase of the patient's respiratory cycle.

In yet a further aspect of the present disclosure, the monitoring of the patient's respiratory cycle is based on sensors located on the patient's chest.

In still a further aspect of the present disclosure, the monitoring of the patient's respiratory cycle is based on a ventilator connected to the patient.

In another aspect of the present disclosure, the method further includes monitoring the patient's respiratory cycle to determine a current phase of the patient's respiratory cycle, and displaying a notification when the current phase of the patient's respiratory cycle does not correspond to the CBCT image data or the additional CBCT image data.

In yet another aspect of the present disclosure, the method further includes identifying the tool in the CBCT image data, orienting the CBCT image data based on a position and orientation of the tool in the CBCT image data, and displaying the CBCT image data based on the orienting.

In a further aspect of the present disclosure, the tool is an ablation device, and the method further includes identify a radiating portion of the ablation device, determining a projected ablation zone based on the position and orientation of the ablation device and ablation settings, and displaying an indication of the projected ablation zone on the CBCT image data.

In another aspect of the present disclosure, the method further includes determining an estimated ablation zone based on the position and orientation of the ablation device, the ablation settings, and an elapsed time, and displaying an indication of the estimated ablation zone on the CBCT image data.

In yet another aspect of the present disclosure, the method further includes receiving fluoroscopic image data of the patient's chest, identifying the tool within the patient's chest in the fluoroscopic image data, and overlaying the CBCT image data onto the fluoroscopic image data based on the location of the tool.

Provided in accordance with an embodiment of the present disclosure is a non-transitory computer-readable storage medium storing instructions which, when executed by a processor, cause a computing device to receive first image data of a patient's chest, identify a luminal network in the patient's chest based on the first image data, generate a three-dimensional (3D) model of the luminal network based on the first image data, detect a location of an EM sensor within an electromagnetic (EM) field generated about the patient's chest by an EM field generator, determine a position of a tool within the patient's chest based on the detected location of the EM sensor, cause a display device to display an indication of the position of the tool on the 3D model, receive second image data of the patient's chest, detect a location of the tool within the patient's chest based on the second image data, and update the indication of the position of the tool on the 3D model based on the detected location.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein:

FIGS. 3A-3E show a flowchart of an example method for providing visual guidance for navigating inside a patient's chest, according to an embodiment of the present disclosure;

DETAILED DESCRIPTION

Figure 1:
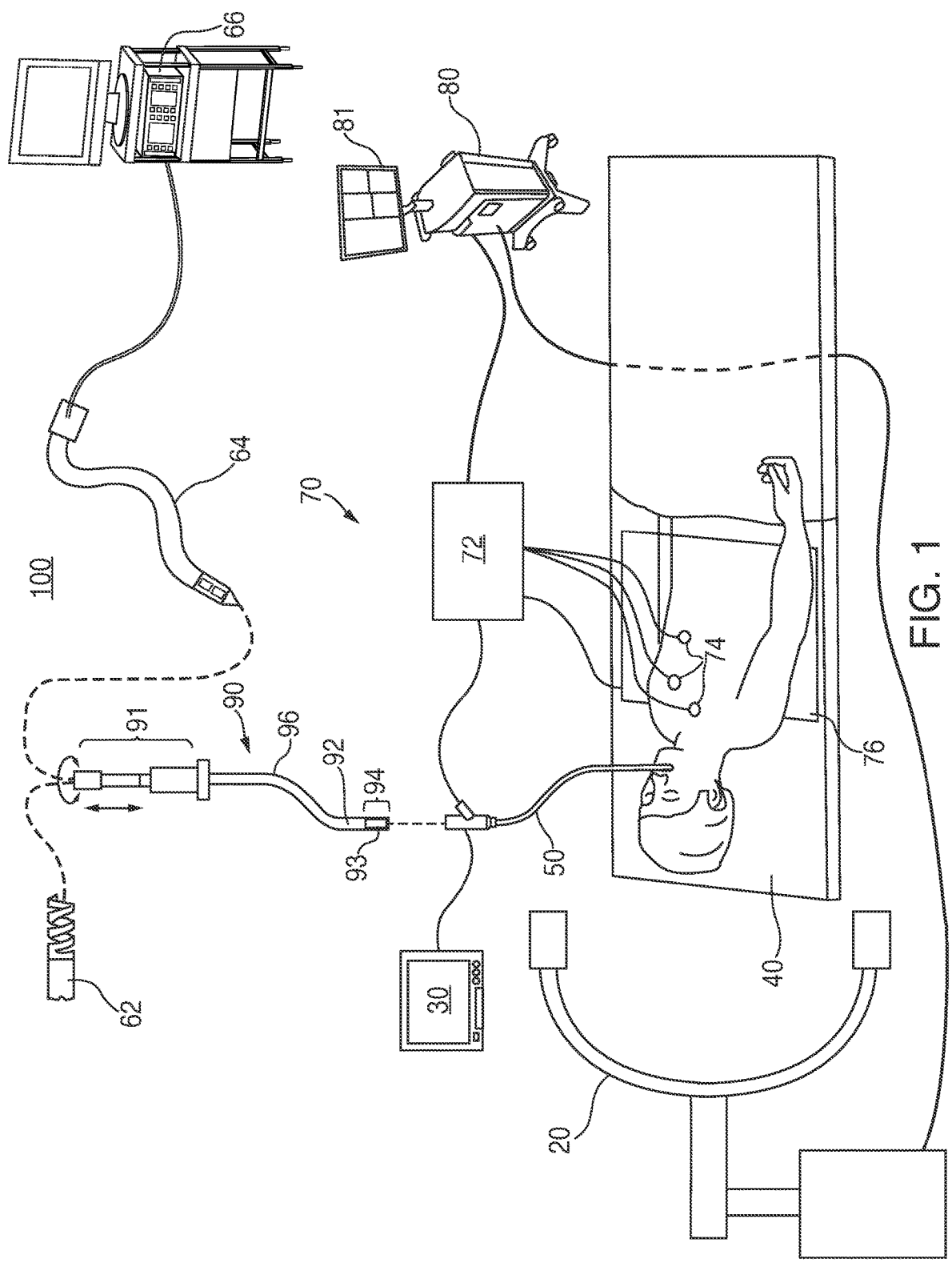
FIG. 1 is a schematic diagram of an endobronchial system for planning and performing treatment of an area of a patient's lungs, according to an embodiment of the present disclosure.

The present disclosure is directed to devices, systems, and methods for using cone beam computed tomography (CBCT) images while navigating tools in a patient's lungs and performing treatment in the patient's lungs. More particularly, the disclosure relates to integrating CBCT image data with a lung navigation system to update and/or improve localization and visualization of treatment targets and tools within the patient's lungs, and to update image-based guidance for a treatment procedure. The CBCT image data may be displayed in conjunction with or alongside a digital reconstruction, such as a three-dimensional (3D) model or map, of the patient's lungs, as well as image data from other imaging modalities including computed tomography (CT) images, magnetic resonance (MR) images, positron emission tomography (PET) images, fluoroscopic and other X-ray type images, and/or ultrasound images. The 3D model may be constructed based on preoperative image data from one or more of the aforementioned imaging modalities. Alternatively or in addition, a CBCT scan performed at the start of the treatment procedure, which may also be used for registration purposes as further described below, may further be used for constructing and/or enhancing the 3D model.

To create the 3D model, a preoperative segmental and subsegmental delineation and extrapolation may be performed based on image data of the patient's lungs to create a visual representation of the patient's lungs, including lumens, pleural surfaces and fissures of the patient's lungs, and/or tumors or other aberrant structures that may be present in the patient's lungs. The delineation may be performed using one or more software applications executing on a computer. The application may generate the 3D model of the patient's lungs based on radiographically obtained image data, noted above, to use for the visual representation of the patient's lungs.

The 3D model may show, among other things, the lumens, pleural surfaces and fissures, and other structures of the patient's lungs. The image data may further be processed to identify one or more treatment targets, such as tumors or other aberrant structures, in the patient's lungs. For example, the application may identify the locations of lumens, such as airways, blood vessels, and/or lymphatic structures from the image data, and, based on the locations of the lumens, determine where lung fissures are located and a degree of completeness of the fissures, as well as determine the locations of the pleural surfaces and/or treatment targets. The 3D model and image data may then be viewed by a clinician and/or surgeon to plan a medical treatment procedure, such as a surgical or interventional procedure. The 3D model and/or treatment plan may further be stored for later viewing during the treatment procedure in an operating room or the like.

As described further below, the treatment plan may include identified locations for one or more treatment targets, such as tumors, lesions, or other aberrant structures identified in the image data, and a pathway between the patient's trachea and each of the treatment targets. The pathway may include a portion located inside lumens, such as airways, of the patient's lungs, and a portion located outside of the airways of the patient's lungs. An "exit point" may mark the transition point between the portion of the pathway located inside the patient's airways and the portion of the pathway located outside of the patient's airways.

During the treatment procedure, the 3D model may be displayed, as further described below, to assist the clinician in navigating one or more tools to the treatment target. The 3D model may include an indicator of a tracked position of the tool inside the patient's lungs. At various times during the treatment procedure, additional image data, such as the CBCT data described above, may be collected to show a real-time location of the tool and/or the treatment target in the patient's lungs. For example, after the tool passes the "exit point" and is located outside of the patient's airways, or at any other time of the clinician's choosing, a CBCT scan may be performed and the collected data processed to identify the tool and/or the treatment target. The indicator on 3D model of the tracked position of the tool may then be updated based on the image data collected from the CBCT scan, thereby showing a confirmed location of the tool and/or the treatment target. The image data collected from the CBCT scan may further show, and thus provide a software application the ability to track, the location of the tool during various phases of the patient's respiration cycle. While the 3D model may be generated based on image data acquired while the patient was in a particular phase of the respiration cycle, e.g. full breath hold, the patient will not be maintaining that phase of the respiration cycle for the entire duration of the treatment procedure. Thus, acquiring image data during the treatment procedure, during various phases of the patient's respiration cycle, particularly during normal tidal volume breathing, may provide a clearer and more accurate visualization of the location of the tool and the treatment target inside the patient's lungs, as well as the position of the treatment tool relative to the treatment target. As such, the intra-procedural CBCT scan may be used to confirm placement of the tool at the treatment target.

The methods, systems, devices, and computer-readable media described herein are useful in various planning and/or navigation contexts for treatment procedures performed on the patient's lungs and surrounding tissue. For example, in an embodiment in which a clinician is performing treatment of an area of the patient's lungs, the methods and systems may provide the clinician with various views of the patient's lungs and the location of the tool and treatment target therein. Additionally, as will be described in further detail below, the methods and systems may provide the clinician with the ability to update the indicated location of the tool and/or treatment target on the 3D model at a time of the clinician's choosing, by performing one or more intra-operative CBCT scans to collect image data about the location of the tool and/or treatment target in the patient's lungs. These and other aspects of the present disclosure are detailed hereinbelow.

An electromagnetic navigation (EMN) system, such as the ELECTROMAGNETIC NAVIGATION BRONCHOS-COPY® system currently sold by Medtronic PLC under the brand name SUPERDIMENSION®, may be used for planning and performing treatment of an area of a patient's lungs. Generally, in an embodiment, the EMN system may be used in planning treatment of an area of the patient's lungs by identifying the locations of one or more treatment targets in the patient's lungs, selecting one or more of the treatment targets as a target location, determining a pathway to the target location, navigating a positioning assembly to the target location, and navigating a variety of tools to the target location via the positioning assembly. The EMN system may be configured to display various views of the patient's lungs, including the aforementioned image data and 3D model.

With reference to FIG. 1, an EMN system 100 suitable for implementing methods for providing visual guidance for navigating inside a patient's chest is provided in accordance with the present disclosure. As shown in FIG. 1, EMN system 100 is used to perform one or more procedures on a patient supported on an operating table 40. In this regard, EMN system 100 generally includes a bronchoscope 50, monitoring equipment 30, an electromagnetic (EM) tracking system 70, and a computing device 80.

Bronchoscope 50 is configured for insertion through the patient's mouth and/or nose into the patient's airways. Bronchoscope 50 includes a source of illumination and a video imaging system (not explicitly shown) and is coupled to monitoring equipment 30, for example, a video display, for displaying the video images received from the video imaging system of bronchoscope 50. In an embodiment, bronchoscope 50 may operate in conjunction with a catheter guide assembly 90. Catheter guide assembly 90 includes a locatable guide (LG) 92 and an extended working channel (EWC) 96 configured for insertion through a working channel of bronchoscope 50 into the patient's airways (although the catheter guide assembly 90 may alternatively be used without bronchoscope 50). Catheter guide assembly 90 includes a handle 91 connected to EWC 96, and which can be manipulated by rotation and compression to steer LG 92 and EWC 96. EWC 96 is sized for placement into the working channel of bronchoscope 50. In the operation of catheter guide assembly 90, LG 92, including an EM sensor 94, is inserted into EWC 96 and locked into position such that EM sensor 94 extends a desired distance beyond a distal tip 93 of EWC 96. The location of EM sensor 94, and thus distal tip 93 of EWC 96, within an EM field generated by EM field generator 76, can be derived by tracking module 72 and computing device 80. For a more detailed description of catheter guide assembly 90, reference is made to commonly-owned U.S. Pat. No. 9,247,992, entitled "MICROWAVE ABLATION CATHETER AND METHOD OF UTILIZING THE SAME", filed on Mar. 15, 2013, by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assembly 90 to track a position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes an application 81, where the data from reference sensors 74 are used to calculate a patient coordinate frame of reference.

Although EM sensor 94 is described above as being included in LG 92, it is also envisioned that EM sensor 94 may be embedded or incorporated within a treatment tool, such as a biopsy tool 62 and/or an ablation tool 64, where the treatment tool may alternatively be utilized for navigation without need of LG 92 or the necessary tool exchanges that use of LG 92 requires. EM sensor 94 may also be embedded or incorporated within EWC 96, such as at a distal portion of EWC 96, thereby enabling tracking of the distal portion of EWC 96 without the need for a separate LG 92.

According to an embodiment, treatment tools 62, 64 are configured to be insertable into catheter guide assembly 90 following navigation to a target location and removal of LG 92. Biopsy tool 62 may be used to collect one or more tissue samples from the target location, and in an embodiment, is further configured for use in conjunction with tracking system 70 to facilitate navigation of biopsy tool 62 to the target location, and tracking of a location of biopsy tool 62 as it is manipulated relative to the target location to obtain the tissue sample. Ablation tool 64 is configured to be operated with a generator 66, such as a radio frequency generator or a microwave generator, and may include any of a variety of ablation tools and/or catheters, examples of which are more fully described in U.S. Pat. Nos. 9,259,269; 9,247,993; 9,044,254; 9,370,398; and 9,993,295, all entitled "MICROWAVE ABLATION CATHETER AND METHOD OF USING THE SAME", filed on Mar. 15, 2013, by Ladtkow et al., the entire contents of each of which is incorporated herein by reference. Though shown as a biopsy tool and microwave ablation tool in FIG. 1, those of skill in the art will recognize that other tools including for example RF ablation tools, brachytherapy tools, and others may be similarly deployed and tracked without departing from the scope of the present disclosure. Additionally, a piercing tool and/or puncture tool may be used and/or incorporated within LG 92 to create an exit point where LG 92, and thereby EWC 96, is navigated outside of the patient's airways and toward the target location, as further described below.

A radiographic imaging device 20, such as a C-arm imaging device capable of performing a CBCT scan of at least a portion of the patient's lungs, may be used in conjunction with EMN system 100. Imaging device 20 may further be capable of performing fluoroscopic scans of the patient's lungs. As shown in FIG. 1, imaging device 20 is connected to computing device 80 such that application 81 may receive and process image data obtained by imaging device 20. However, imaging device 20 may also have a separate computing device located within the treatment room or in a separate control room to first receive the image data obtained by imaging device 20 and relay such image data to computing device 80. For example, to avoid exposing the clinician to unnecessary radiation from repeated radiographic scans, the clinician may exit the treatment room and wait in an adjacent room, such as the control room, while imaging device 20 performs the CBCT and/or fluoroscopic scans.

Computing device 80 includes software and/or hardware, such as application 81, used to facilitate the various phases of an EMN procedure, including generating the 3D model, identifying a target location, planning a pathway to the target location, registering the 3D model with the patient's actual airways, navigating to the target location, and performing treatment at the target location. For example, computing device 80 utilizes data acquired from a CT scan, CBCT scan, magnetic resonance imaging (MRI) scan, positron emission tomography (PET) scan, and/or any other suitable imaging modality to generate and display the 3D model of the patient's airways, to enable identification of a target location on the 3D model (automatically, semi-automatically or manually) by analyzing the image data and/or 3D model, and allow for the determination and selection of a pathway through the patient's airways to the target location. While the image data may have gaps, omissions, and/or other imperfections included in the image data, the 3D model is a smooth representation of the patient's airways, with any such gaps, omissions, and/or imperfections in the image data filled in or corrected. The 3D model may be presented on a display monitor associated with computing device 80, or in any other suitable fashion. An example of the planning software described herein can be found in U.S. Pat. Nos. 9,459,770, 9,925,009, and 9,639,666, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. Pat. No. 9,770,216, entitled "SYSTEM AND METHOD FOR NAVIGATING WITHIN THE LUNG", filed on Jun. 29, 2015, by Brown et al., the contents of which are incorporated herein by reference.

Using computing device 80, various views of the image data and/or 3D model may be displayed to and manipulated by a clinician to facilitate identification of the target location. As noted above, the target location may be a site within the patient's lungs where treatment is to be performed. For example, the treatment target may be located in lung tissue adjacent to an airway. The 3D model may include, among other things, a model airway tree corresponding to the actual airways of the patient's lungs, and show the various passages, branches, and bifurcations of the patient's actual airway tree. Additionally, the 3D model may include lesions, markers, blood vessels and vascular structures, lymphatic vessels and structures, organs, other physiological structures, and/or a 3D rendering of the pleural surfaces and fissures of the patient's lungs. Some or all of the aforementioned elements may be selectively displayed, such that the clinician may choose which elements should be displayed when viewing the 3D model.

After identifying the target location, application 81 may determine a pathway between the patient's trachea and the target location via the patient's airways. In instances where the target location is located in lung tissue that is not directly adjacent an airway, at least a portion of the pathway will be located outside of the patient's airways to connect an exit point on an airway wall to the target location. In such instances, LG 94 and EWC 96 will first be navigated along a first portion of the pathway through the patient's airways to the exit point on the airway wall. LG 94 may then be removed from EWC 96 and an access tool, such as a piercing or puncture tool, inserted into EWC 96 to create an opening in the airway wall at the exit point. EWC 96 may then be advanced through the airway wall into the parenchyma surrounding the airways. The access tool may then be removed from EWC 96 and LG 94 and/or tools 62, 64 reinserted into EWC 96 to navigate EWC 96 along a second portion of the pathway outside of the airways to the target location.

During a procedure, EM sensor 94, in conjunction with tracking system 70, enables tracking of EM sensor 94 (and thus distal tip 93 of EWC 96 or tools 62, 64) as EM sensor 94 is advanced through the patient's airways following the pathway planned during the planning phase. As an initial step of the procedure, the 3D model is registered with the patient's actual airways to enable application 81 to display an indication of the location of EM sensor 94 on the 3D model corresponding to the location of EM sensor 94 within the patient's airways.

One potential method of registration involves performing a survey of the patient's lungs by navigating LG 92 into each lobe of the patient's lungs to at least the second bifurcation of the airways of that lobe. The position of LG 92 is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. Pat. No. 10,772,532, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures, pleural surfaces, and fissures of the lungs are accurately determined.

Another potential method of registration uses image data from a CBCT scan performed at the start of the treatment procedure to generate the 3D model with the patient remaining on table 40 while the clinician performs the above-described planning phase. Because the scan is taken with reference sensors 74 placed on the patient, the anatomy of the patient relative to reference sensors 74 is known. By performing the scan with reference sensors 74 placed on the patient, performing registration by using the lung survey technique, described above, becomes unnecessary. Additionally, features and sensors in EM field generator 76 under the patient may also be used as another means to help ensure the target location is placed within the ENB field. The clinician may then start the navigation phase of the procedure without performing the above-described survey of the patient's lungs because the patient will still be in substantially the same position as the patient was when the image data on which the 3D model is based were obtained. Thus, application 81 may extrapolate sufficient data points from the position of EM sensor 94 within the EM field while LG 92 is navigated along the planned pathway to register the 3D model to the patient's actual airways while the navigation phase is in process.

At various times during the procedure, the clinician may request that additional CBCT scans be performed on the patient. The additional CBCT scans may be directed at a particular location in the patient's body, such as an area of the patient's lungs about the position of LG 92, for which the clinician wants additional image data. For example, the additional image data may be used to confirm the position of EM sensor 94 (representing the location of LG 92 and/or tool 62, 64) and/or the target location within the patient's lungs. Application 81 may receive the image data acquired by the additional CBCT scan and process the additional image data to identify the position of EM sensor 94 and/or the target location within the patient's lungs. Application 81 may then update the indicator of the position of EM sensor 94 on the 3D model based on the additional CBCT image data if the additional image data indicates that the position displayed based on the original image data is incorrect. In some embodiments, the additional CBCT scans may be performed based on the patient's breathing or respiratory cycle, such as to acquire image data during different phases of the patient's respiratory cycle, as further described below. In addition to CBCT scans, the clinician may also request that fluoroscopic scans be performed at various times during the procedure. Image data acquired from the fluoroscopic scans may further be used to assist the clinician in navigating and positioning LG 92 about the target location.

Figure 2:
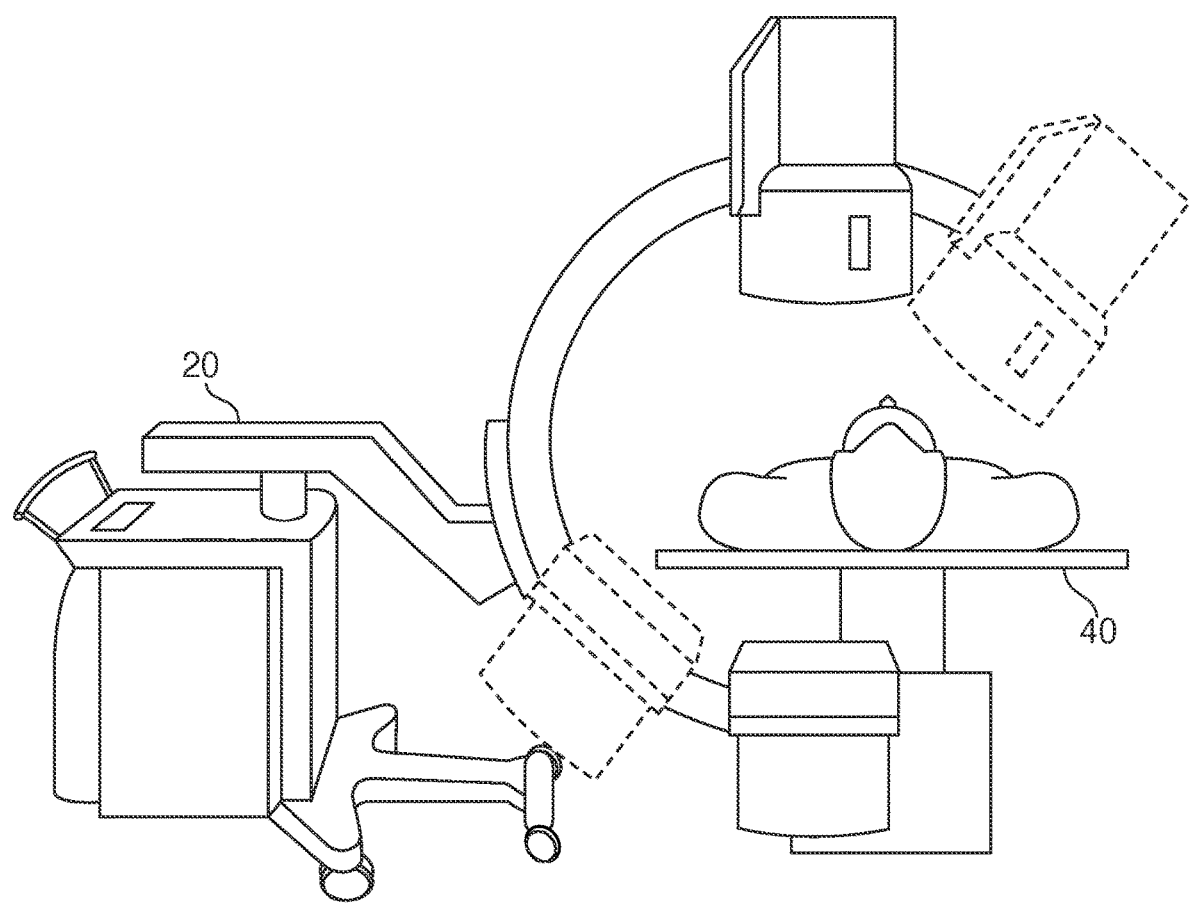
FIG. 2 is a schematic diagram of an imaging device usable with the system of FIG. 1 shown in relation to the patient.

Turning now to FIG. 2, wherein the patient is shown laying on table 40 with imaging device 20 positioned for performing scan of a portion of the patient's body. As further described below, application 81 may provide guidance regarding how to position imaging device 20 when an additional scan is requested during the procedure. Thus, imaging device 20 may be moved out of position during the procedure to allow the clinician better access to the patient, and may be moved back into position for scanning with guidance provided by application 81.

With reference to FIGS. 3A-3E, there is shown a flowchart of an exemplary method 300 for providing visual guidance for navigating inside a patient's chest, according to embodiments of the present disclosure. As described below, various subsections of method 300 may be directed at different embodiments. Thus, those skilled in the art will recognize that while presented and described as an ordered flow, various steps of method 300 may be omitted or performed in a different order than described below.

Figure 3A:
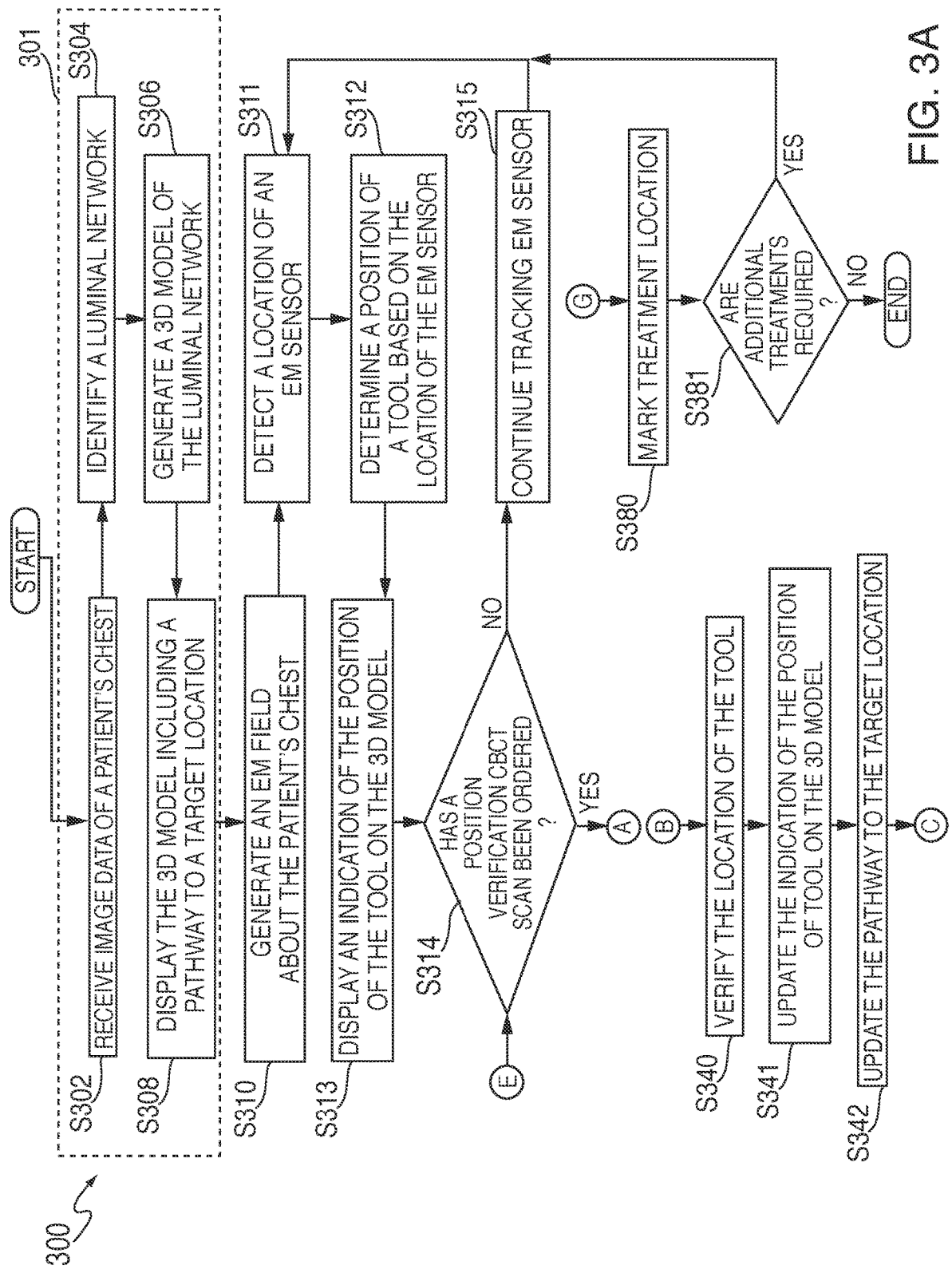

Starting with FIG. 3A, an initial portion 301 of method 300 includes the steps of the above-described planning phase of the treatment procedure. Thus, method 300 may start at step S302 where application 81 receives image data of the patient's chest. The image data may be acquired during a pre-procedure scan of the patient's body, or a relevant portion thereof, such as a CT scan, MM scan, PET scan, CBCT scan, etc. Alternatively, the image data may be acquired during a scan, such as a CBCT scan, performed at the start of the treatment procedure.

After receiving the image data, application 81 processes the image data, at step S304, to identify a luminal network in the image data. The luminal network may be the patient's airways, blood vessels, and/or lymphatic vessels in the patient's lungs. Application 81 may further process the image data to identify other structures, such as the pleura and fissures of the patient's lungs, other organs and critical structures, and/or aberrant structures in and/or around the patient's lungs. Application 81 then, at step S306, generates a 3D model based on the processed image data. Based on the image data and/or the 3D model, at least one treatment target is identified, either automatically by application 81, semi-automatically with input from the clinician, or manually by the clinician. After identifying the treatment target, a target location representative of the identified location of the treatment target is marked on the 3D model, and application 81 determines a pathway between the patient's trachea and the target location via the patient's airways.

As noted above, the pathway may include various portions, including at least one portion located inside the patient's airways running between the trachea and an exit point in an airway wall proximate the target location, and at least one portion located outside the patient's airways running from the exit point to the target location. The pathway represents a recommended route along which LG 92 or other tool including sensor 94 should be navigated through the patient's airways and, as described further below, after reaching the exit point, through the tissue and space surrounding the patient's airways. Application 81 displays the pathway and the target location on the 3D model at step S308.

Next, the navigation phase of the treatment procedure commences. As an initial task, the 3D model must be registered to the actual airways of the patient's lungs. As described above, there are various methods of registration that may be used for this purpose, including the lung survey method described above. Alternatively, as also mentioned above, if the 3D model is generated based on image data from a CBCT scan performed at the start of the treatment procedure, and the patient remains in substantially the same position on table 40 during the above-described planning phase, a lung survey may not be necessary, because application 81 may collect sufficient data points regarding the position of LG 92 in the patient's airways during the initial portion of the navigation phase to register the 3D model to the patient's airways while navigation is in progress.

To start this process, at step S310, EM field generator 76 generates an EM field about the patient's chest. An EM sensor 94, whether included in LG 92, tools 62, 64, and/or directly in EWC 96, is then inserted into the patient's airways and a location of EM sensor 94 in the EM field is detected by tracking system 70 at step S311. The detected location of EM sensor 94 is relayed to application 81 to determine, at step S312, a position of LG 92, tools 62, 64, and/or EWC 96 based on the detected location of EM sensor 94. As mentioned herein, the detected position of EM sensor 94 may be reflective of whichever tool EM sensor 94 is included in, such as LG 92, tools 62, 64, and/or EWC 96, but for purpose of brevity and to ease this description, an example wherein LG 92 is used for navigation will be described hereinafter. However, those skilled in the art will realize that any of the other aforementioned tools and devices including an EM sensor 94 could be substituted for LG 92.

Figure 4:
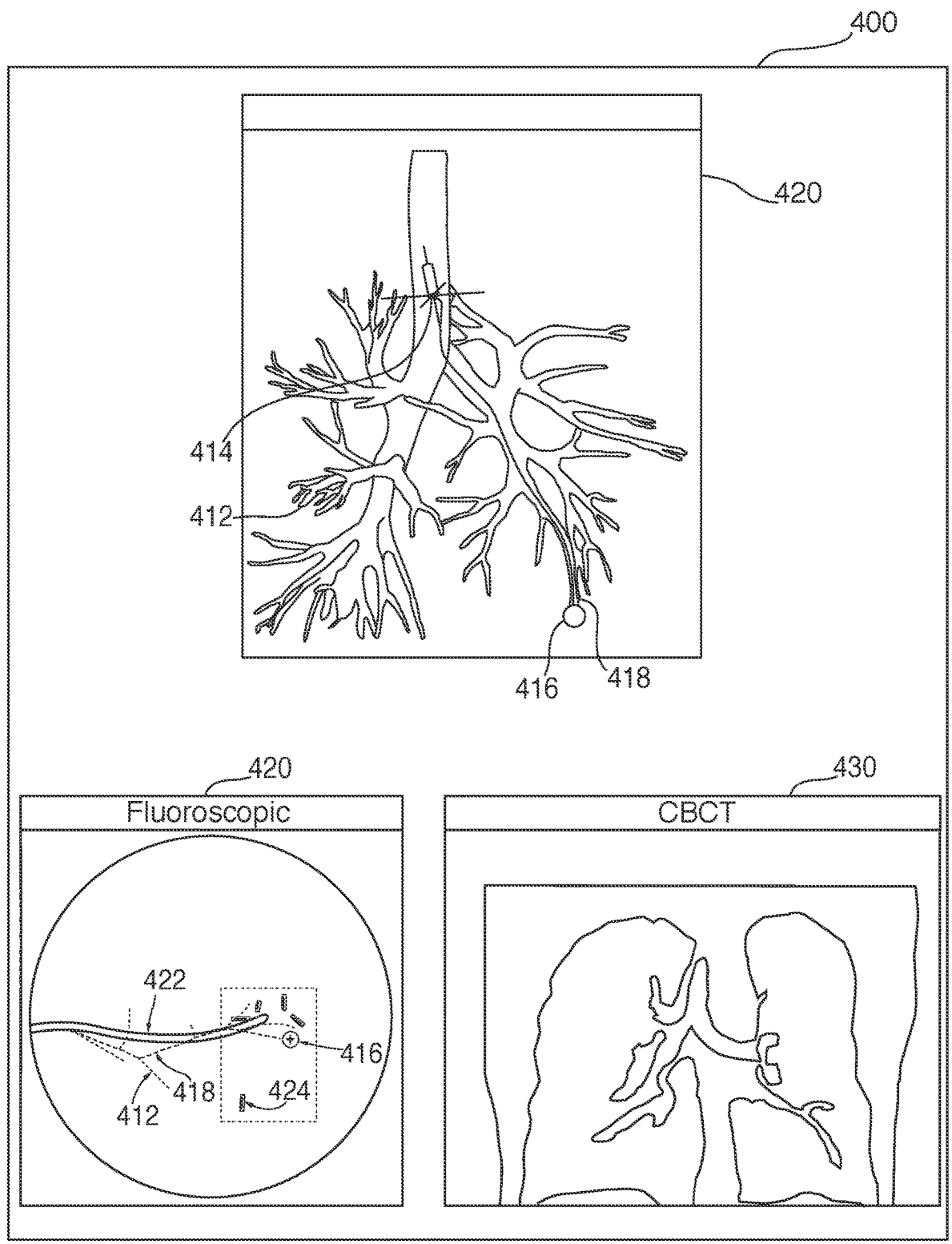
FIG. 4 shows an exemplary user interface which may be presented as part of the method of FIGS. 3A-3E.

Next, at step S313, Application 81 displays an indication of the determined position of LG 92 on the 3D model. For example, as shown in FIG. 4 (described below), a view 410 of the 3D model includes at least an airway tree 412, an indicator 414 of the determined position of LG 92, the target location 416, and the pathway 418 to the target location. Steps S311 to S313 may be iteratively repeated while navigation is in progress to continually detect the location of EM sensor 94 in the EM field, and determine and display a corresponding location of LG 92 on the 3D model.

As noted above, the clinician may, at various times during the procedure, request that an intra-procedural CBCT scan be performed to verify the determined position of LG 92. For example, the clinician may request that a CBCT scan be performed when LG 92 reaches the exit point where the pathway moves from within the patient's airways to outside of the patient's airways. The clinician may also request that a CBCT scan be performed after LG 92 has been navigated through the airway wall and towards the target location outside of the patient's airways. Further, the clinician may request that a CBCT scan be performed to confirm the location of LG 92 when LG 92 is navigated proximate the target location, such as to confirm placement of LG 92 at the treatment target. Thus, application 81 determines, at step S314, whether a request, such as a button press or other user input, for a CBCT scan has been received. If a request for a CBCT scan has not been received, application 81 continues tracking the location of EM sensor 94 at step S315, whereafter processing returns to step S311. However, if application 81 determines that a request for a CBCT scan has been received, processing proceeds to step S320.

Figure 3B:
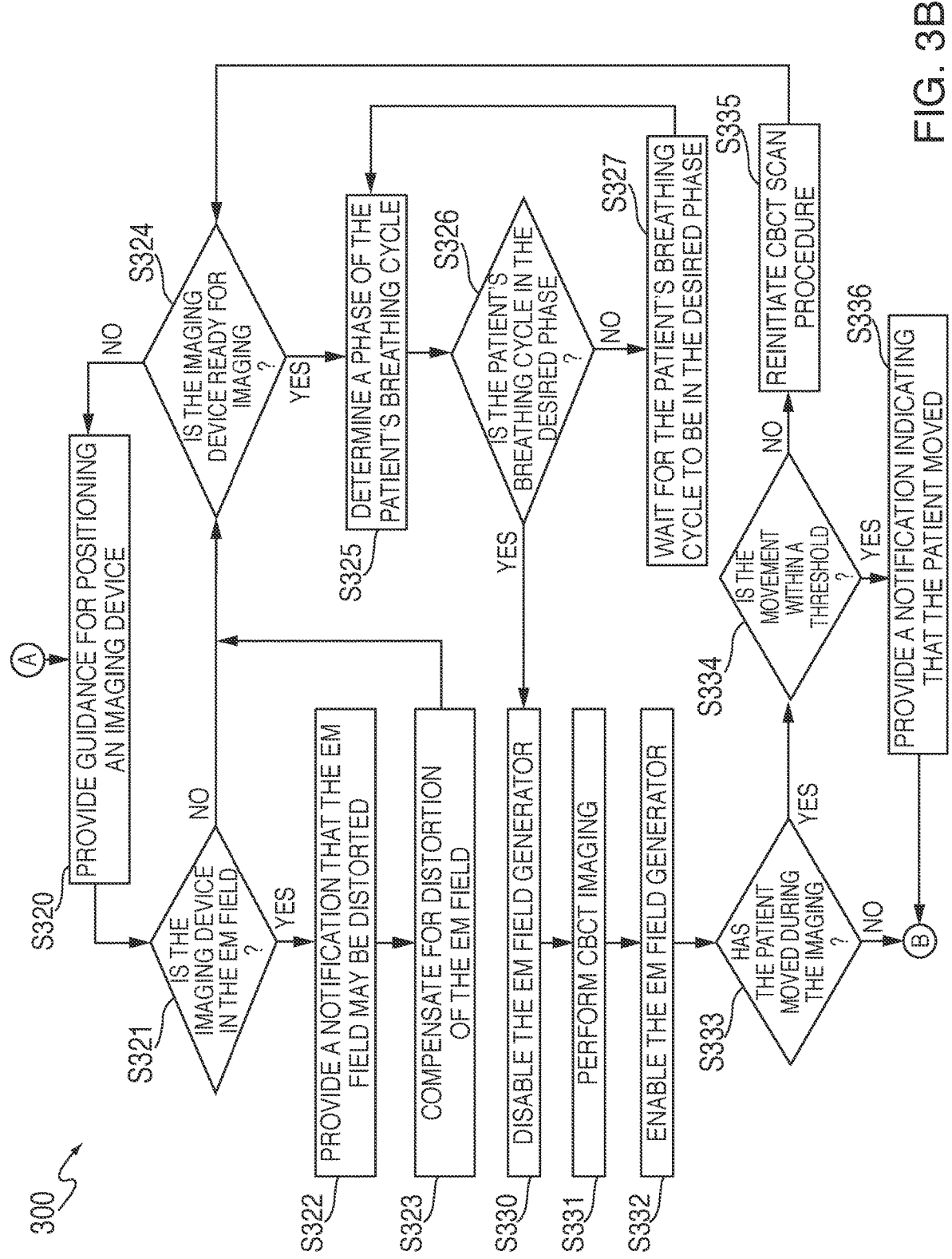

Turning now to FIG. 3B, there is shown a portion of method 300 relating to a CBCT imaging process. Thus, after a CBCT scan has been requested, application 81, at step S320, provides guidance for positioning imaging device 20. The guidance may instruct the clinician how to position imaging device 20 to perform a CBCT scan of at least a portion of the patient's chest based on the determined location of LG 92. Thus, a focused CBCT scan may be performed of only the area surrounding the determined location of LG 92, thereby limiting the amount of radiation exposure to the patient. For example, application 81 may provide visual guidance, such as graphical illustrations, and/or audible instructions regarding positioning of imaging device 20. Thereafter or concurrently therewith, at step S321, application 81, based at least in part on data received from tracking system 70, determines whether imaging device 20 is within the EM field generated by EM field generator 76.

If imaging device 20 is within the EM field, application 81 may provide a notification, at step S322, informing the clinician that the EM field may be distorted, such as by metal and/or other EM components included in imaging device 20 being present in the EM field. The notification may be a visual and/or audio notification, and may alert the clinician that the displayed location of LG 92 may be incorrect due to the distortion of the EM field. Application 81 and/or tracking system 70 may then, at step S323, compensate for the distortion of the EM field, such as by adjusting the EM field and/or the displayed position of LG 92 on the 3D model based on the distortion of the EM field.

Thereafter, or if application 81 determines at step S321 that imaging device 20 is not in the EM field, processing proceeds to step S324 where application 81 determines whether the imaging device is ready for imaging. In some embodiments, application 81 may be able to actively track the location of imaging device 20, such as by sensors included in imaging device 20. Alternatively, application 81 may determine whether imaging device 20 is ready for imaging based on input from the clinician. If application 81 determines that imaging device 20 is not yet ready for imaging, processing returns to step S320. Alternatively, if application 81 determines that imaging device 20 is ready for imaging, processing proceeds to step S325, where application 81 determines a current phase of the patient's respiratory cycle. The current phase of the patient's respiratory cycle may be determined based on data received from sensors, such as reference sensors 74 located on the patient's chest. Further information on determination of a patient's respiratory cycle and compensation for movement occurring during the patient's respiratory cycle may be found in commonly-owned co-pending U.S. Patent Publication No. 2018/0055576, entitled RESPIRATION MOTION STABILIZATION FOR LUNG MAGNETIC NAVIGATION SYSTEM, filed on Sep. 1, 2016, by Koyrakh et al., the entire contents of which are incorporated herein by reference. Alternatively, or in addition, the current phase of the patient's respiratory cycle may be determined based on data received from a ventilator coupled to the patient. The clinician may request that the CBCT scan be performed during a particular desired phase of the patient's respiratory cycle, such as full breath hold, full exhale, etc. Therefore, at step S326, application 81 determines whether the current phase of the patient's respiratory cycle corresponds to the desired phase of the patient's respiratory cycle requested by the clinician. If application 81 determines that the current phase of the patient's respiratory cycle does not correspond to the desired phase, the method proceeds to step S327, where application 81 waits for the patient's respiratory cycle to enter the desired phase. Thereafter, processing returns to step S325 to again determine the current phase of the patient's respiratory cycle. If application 81 determines that the current phase of the patient's respiratory cycle corresponds to the desired phase, processing proceeds to step S330.

At step S330, application 81 causes tracking system 70 to disable EM field generator 76 to avoid interference with imaging device 20 during the imaging process. Thereafter, at step S331, the CBCT imaging is performed. The CBCT imaging may be performed manually by the clinician interacting with imaging device 20 to perform the CBCT imaging. Alternatively, the CBCT imaging may be performed automatically or semi-automatically via application 81 directly or indirectly controlling imaging device 20. After the CBCT imaging is complete, detected either based on input from the clinician or based on a signal received from imaging device 20, processing proceeds to step S332 where application 81 causes tracking system 70 to re-enable EM field generator 76.

Thereafter, application 81 determines, at step S333, whether the patient moved during the CBCT imaging process. The determination may be based on data received from sensors, such as reference sensors 74, indicating the patient's current position relative to the patient's position prior to the CBCT imaging, and/or indicating movement of the patient during the CBCT imaging process. If application 81 determines that the patient moved during the CBCT imaging process, application 81 determines, at step S334, whether an amount of the movement is within a predetermined threshold. For example, mere minor movement may be insufficient to affect the CBCT image data collected during the CBCT imaging process, while more significant movement may cause the CBCT image data to be unusable. Therefore, if application 81 determines that the movement is not within the predetermined threshold, and thus exceeds the predetermined threshold, application 81 may mark the CBCT image data received from imaging device 20 after the CBCT imaging as unusable, and reinitiate the CBCT imaging process at step S335, whereafter processing returns to step S324. Alternatively, if application 81 determines that the movement is within the predetermined threshold, application 81 may provide a notification at step S336, indicating that the patient moved but that the movement was within the predetermined threshold. Thereafter, or if application determined at step S333 that the patient did not move during the CBCT imaging process, processing proceeds to step S340.

Returning now to FIG. 3A, at step S340, application 81 verifies the location of LG 92 based on the CBCT image data. For example, application 81 may process the CBCT image data received after the CBCT imaging process to identify the patient's airways and the location of LG 92 within the patient's chest. If application 81 determines that the location of LG 92 identified in the CBCT image data does not correspond with the location indicated on the 3D model, application 81 may, at step S341, provide a notification that the indicated location of LG 92 on the 3D model may be incorrect, and update the indicated location of LG 92 on the 3D model. In some embodiments, application 81 may request approval from the clinician prior to updating the indicated location of LG 92 on the 3D model. If application 81 updates the indicated location of LG 92 on the 3D model, application 81 may further update the portion of the pathway between the updated location of LG 92 and the target location. In some embodiments, application 81 may request approval from the clinician prior to updating the pathway. Thereafter, processing proceeds to step S350.

Turning now to FIG. 3C, there is shown a portion of method 300 relating to display of the CBCT image data obtained during the CBCT imaging process. At step S350, application 81 again determines a current phase of the patient's respiratory cycle, similar to the determination performed at step S325. Thereafter, at step S351, application 81 determines whether CBCT image data corresponding to the current phase of the patient's respiratory cycle is available. If application 81 determines that CBCT data corresponding to the current phase of the patient's respiratory cycle is not available, application 81 provides a notification at step S353 that CBCT image data corresponding to the current phase of the patient's respiratory cycle is not available. Thereafter, at step S354, application 81 selects predetermined CBCT image data. In an embodiment, application 81 may select CBCT image data corresponding to the phase towards which the patient's respiratory cycle is moving. For example, if the patient's respiratory cycle is currently past full inhale and partially into an exhaling phase, application 81 may select CBCT image data corresponding to a portion of the exhaling phase towards which the patient's respiratory cycle is moving. In another embodiment, application 81 may select the most recently obtained CBCT image data. Thereafter, processing proceeds to step S355.

If application 81 determined at step S351 that CBCT image data corresponding to the current phase of the patient's respiratory cycle is available, application 81 selects such CBCT image data at step S352. At step S355, application 81 identifies LG 92 in the CBCT image data, similar to the identification of LG 92 at step S341. Application 81 further determines a position and orientation of LG 92 based on the CBCT image data, and orients the CBCT image data based on the determined position and orientation of LG 92 at step S356. Application 81 then displays the CBCT image data at step S357, as shown in view 430 of FIG. 4, described below. Thereafter, at step S358, application 81 determines whether LG 92 has been placed at the target location. The determination may be based on processing of the CBCT image data, tracking data received from tracking system 70, and/or input provided by the clinician. If application 81 determines that LG 92 has not yet been placed at the target location, or if application 81 cannot determine that LG 92 has been placed at the target location, or if application 81 determines, such as based on input provided by the clinician, that an alternative view is necessary to determine if LG 92 has been placed at the target location, processing proceeds to step S360.

Turning now to FIG. 3D, there is shown a portion of method 300 relating to a fluoroscopic imaging process. At step S360, application 81 determines whether fluoroscopic image data has been received. If fluoroscopic image data has not been received, processing returns to step S314, whereafter the CBCT imaging process may be repeated or navigation may continue. However, if fluoroscopic image data has been received, processing proceeds to step S361, where application 81 identifies LG 92 in the fluoroscopic image data. Thereafter, at step S362, application 81 registers the CBCT image data and the fluoroscopic image data.

Application 81 then, at step S363, displays the CBCT image data in conjunction with the fluoroscopic image data. In an embodiment, application 81 may display the CBCT image data as an overlay onto the fluoroscopic image data, as shown in view 420 of FIG. 4, described below. In such embodiment, the overlay of the CBCT data onto the fluoroscopic image data gives the clinician greater insight into the actual location of LG 92 within the patient's chest. The CBCT image data may also be displayed according to the patient's breathing cycle. For example, the CBCT image data may be displayed as an overlay onto the fluoroscopic image data, and faded in and out as the patient breathes, thus becoming clearer when the patient's breathing cycle coincides with the phase of the breathing cycle during which the CBCT image data was taken, and less clear when the patient's breathing cycle moves to the next phase.

Thereafter, at step S364, application 81 again determines whether LG 92 has been placed at the target location. As with step S358 described above, the determination may be based on processing of the CBCT image data, tracking data received from tracking system 70, and/or input provided by the clinician. If application 81 determines that LG 92 has not been placed at the target location, or if application 81 cannot determine that LG 92 has been placed at the target location, processing returns to step S314 for further imaging and/or navigation.

Alternatively, if application 81 determines at either step S358 or step S364 that LG 92 has been placed at the target location, processing proceeds to step S359 (FIG. 3C). After confirming that LG 92, and thus EWC 96, has been placed at the target location, the clinician may uncouple LG 92 and EWC 96, and remove LG 92 from the patient's airways while leaving EWC 96 in place. Biopsy tool 62 and/or ablation tool 64 may then be inserted into the patient's airways and advanced through EWC 96 to the treatment target at the target location. As described above, in some embodiments, EM sensor 94 may be included in biopsy tool 62 and/or ablation tool 64, thus making such a tool exchange unnecessary. After tool exchanges are complete, or in embodiments where tool exchanges are unnecessary, application 81 determines whether the inserted tool is a biopsy tool 62 or an ablation tool 64. If application 81 determines that the inserted tool is ablation tool 64, processing proceeds to step S370. Alternatively, if application 81 determines that the inserted tool is biopsy tool 62, processing skips directly to step S380 (FIG. 3A, described below).

Figure 3E:
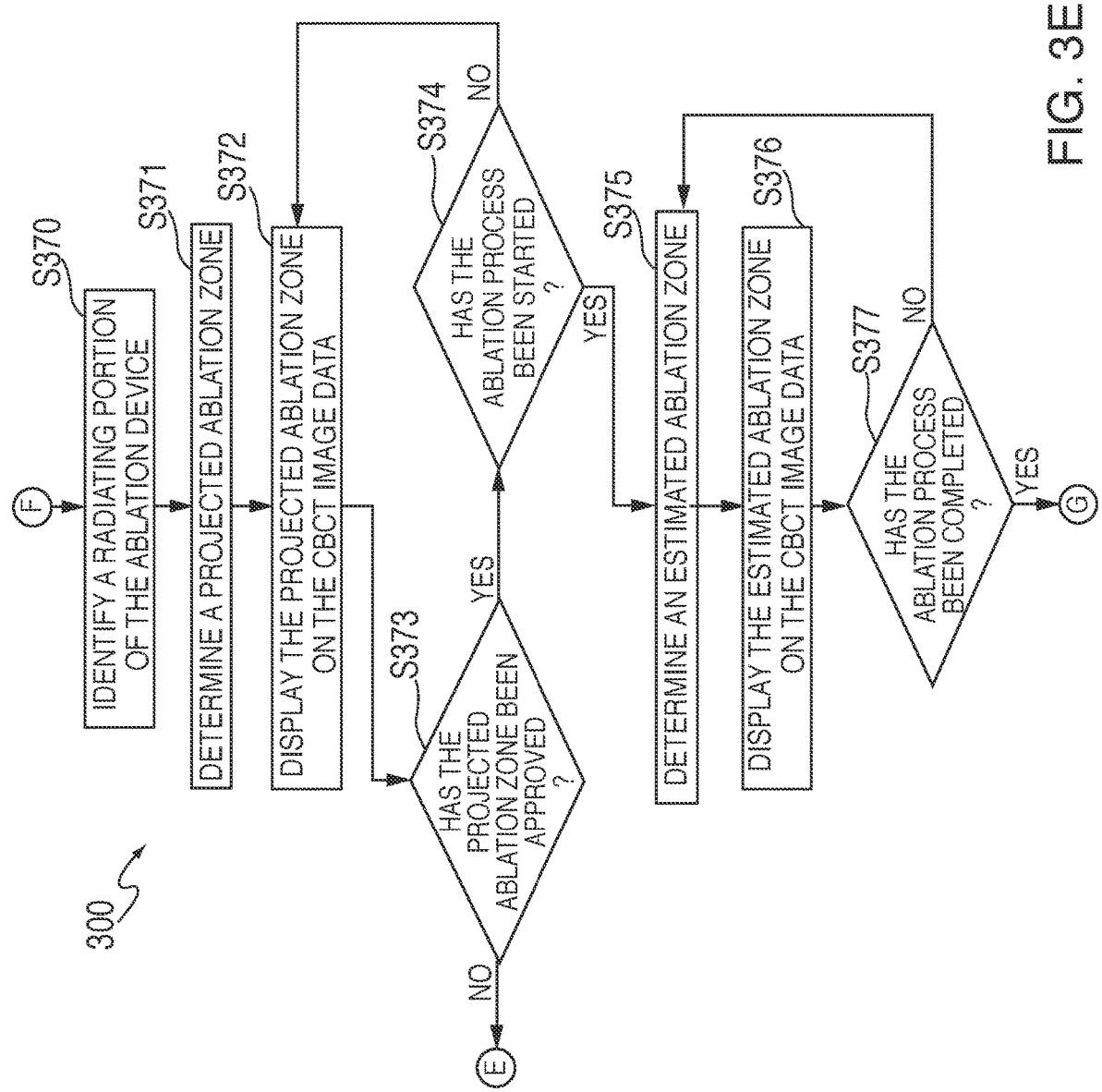

Turning now to FIG. 3E, there is shown a portion of method 300 relating to an ablation procedure. At step S370, application 81 identifies a radiating portion of ablation tool 64 in one or more of the CBCT image data, the fluoroscopic image data, and/or the 3D model. For example, ablation tool 64 may include one or more radiopaque elements about the radiating portion of ablation tool 64 that may be detectable by application 81 while processing CBCT and/or fluoroscopic image data. In another embodiment, application 81 may determine that the radiating portion is a predetermined distance from a distal end of ablation tool 64.

After identifying the radiating portion of ablation tool 64, application 81, at step S371, determines a projected ablation zone based on the location of ablation tool 64, and thus the radiating portion of ablation tool 64, inside the patient's chest, and configuration settings for the ablation procedure. As part of the above-described planning phase, and/or after placement of LG 92 at the target location or at any point prior to step S371, the clinician may enter configuration settings, such as time, temperature, wattage, etc., for the ablation procedure into computing device 80. Application 81 may then, at step S371, use such configuration settings to determine a projected ablation zone representing a maximum area around the radiating portion of ablation tool 64 that will be ablated according to the configuration settings.

Application 81 may then, at step S372, display an indicator of the projected ablation zone on the CBCT image data, the fluoroscopic image data, and/or the 3D model. At step S373, application 81 determines whether the clinician has approved the projected ablation zone. For example, the projected ablation zone may be represented by a sphere surrounding ablation tool 64, with an anchor point of the sphere being the radiating portion of ablation tool 64. Based on the displayed projected ablation zone, the clinician may decide to adjust the configuration settings for the ablation procedure and/or the location of ablation tool 64. For example, based on the displayed projected ablation zone, the clinician may determine that the projected ablation zone does not sufficiently cover the treatment target, and thus choose to adjust the configuration settings or the location of ablation tool 64. The clinician may input a decision to proceed with the ablation procedure or return to navigation into computing device 80. If application 81 determines that the clinician does not approve of the displayed projected ablation zone, processing returns to step S314 for further navigation and/or imaging. Alternatively, if application 81 determines that the clinician approves of the displayed projected ablation zone, processing proceeds to step S374, where application 81 determines whether the ablation process has started. For example, application 81 may detect that an activation button on ablation tool 64 has been depressed. In another embodiment, ablation tool 64 may be controlled by application 81 based on input received from the clinician. Thus, if application 81 determines that the ablation process has not started, processing returns to step S372. Alternatively, if application 81 determines that the ablation process has started, processing proceeds to step S375.

At step S375, application 81 determines an estimated ablation zone. The determination of the estimated ablation zone may be based on the configuration settings for the ablation procedure, the location of the radiating portion of ablation tool 64, an elapsed time since the ablation process was started, and/or additional image data received during the ablation process. For example, application 81 may determine that, based on the configuration settings, after a particular amount of time has elapsed since the ablation process was started, a particular area around the radiating portion of ablation tool 64 would be expected to have been ablated. In another embodiment, additional CBCT and/or fluoroscopic scans may be performed during the ablation process to provide image data showing the progress of the ablation process. Application 81 may then, at step S376, display an indicator of such area, such as by a sphere or other shape around ablation tool 64 in the CBCT image data, the fluoroscopic image data, and/or the 3D model.

Thereafter, at step S377, application 81 determines if the ablation process has been completed. For example, application 81 may determine based on the elapsed time since the ablation process was started reaching the time included in the configuration settings that the ablation process is complete. Application 81 may also receive input from the clinician that the ablation process is complete. If application 81 determines that the ablation process has not been completed, processing returns to step S375. Alternatively, if application 81 determines that the ablation process has been completed, processing proceeds to step S380.

At step S380, application 81 marks the location where treatment, whether biopsy or ablation, was performed. For example, application 81 may store the position information received from tracking system 70 regarding the location of tool 62, 64 in the patient's chest while treatment was performed. In embodiments where an ablation procedure was performed, application 81 may also store the last determined estimated ablation zone of the ablation procedure. Such stored treatment locations and estimated ablation zones may further be displayed on the 3D model.

Next, at step S381, application 81 determines whether additional treatments are required. For example, application 81 may determine based on the above-described treatment plan that additional treatments are required. Application 81 may also receive input from the clinician that additional treatments are required. Thus, if application 81 determines that additional treatments are required, processing returns to step S311. If navigation to a different target location is required, and tool 62, 64 does not include an EM sensor 94, tool 62, 64 may be removed from EWC 96 and replaced by LG 92. Alternatively, if application 81 determines that additional treatments are not required, processing ends.

With reference now to FIG. 4, there is shown an example user interface including the various image data that may be displayed during performance of the treatment procedure described above. FIG. 4 depicts a graphical user interface (GUI) 400 including at least three image views: a 3D model view 410, a fluoroscopic image view 420, and a CBCT image view 430. 3D model view 410 includes at least airway tree 412, tool indicator 414 representing the location of EM sensor 94 in the patient's airways, target location 416, and pathway 418. Each of views 410, 420, and 430 may be selectively enabled and configured to show image data from the various sources described above, according to the clinician's preference.

Figure 5:
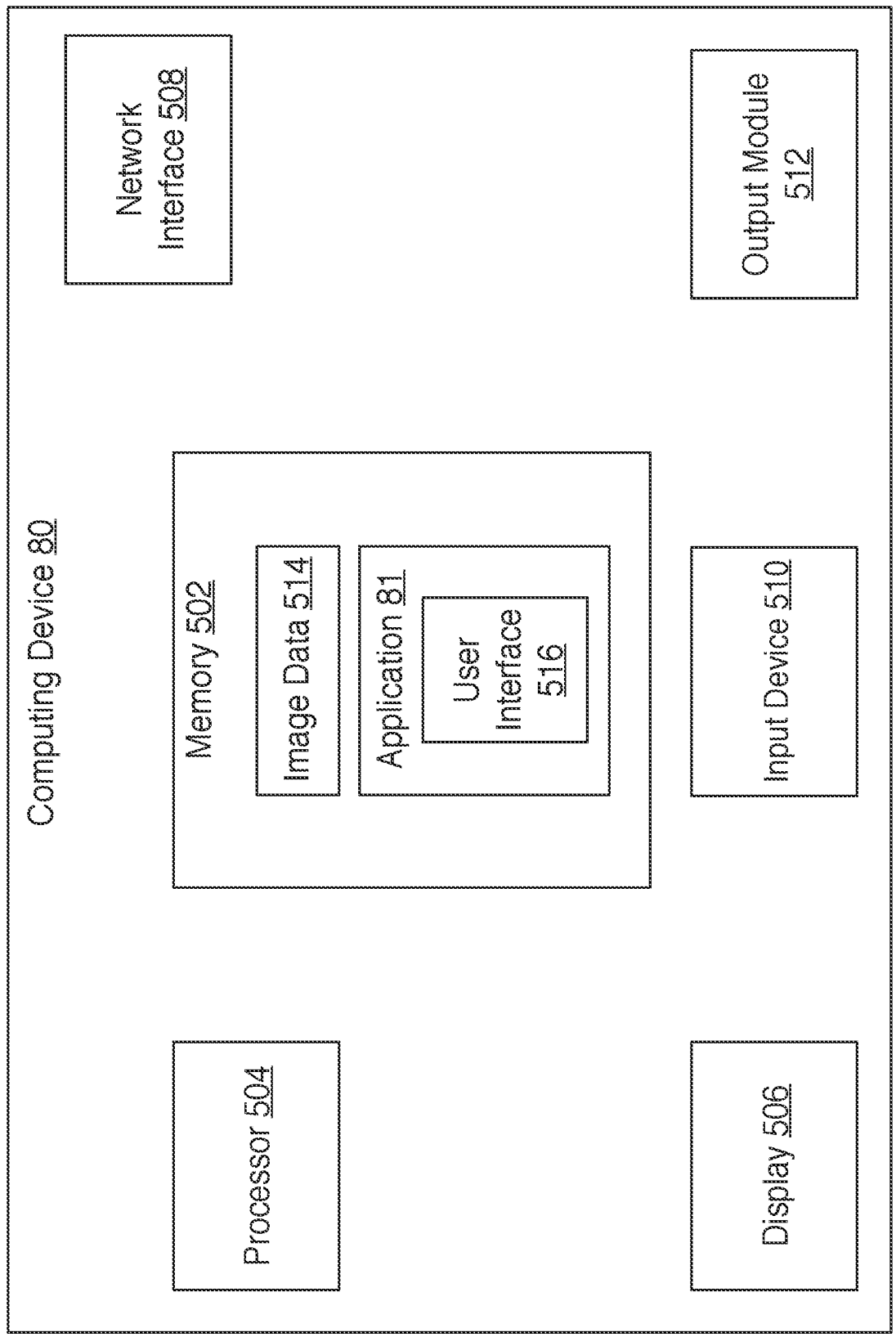
FIG. 5 is a block diagram of an example computing device forming part of the systems of FIG. 1, according to an embodiment of the present disclosure.

Turning now to FIG. 5, there is shown a simplified block diagram of computing device 80. Computing device 80 may include a memory 502, a processor 504, a display 506, a network interface 508, an input device 510, and/or an output module 512. Memory 502 may store application 81 and/or image data 514. Application 81 may, when executed by processor 504, cause display 506 to present user interface 516. Application 81 may also provide the interface between the sensed position of EM sensor 94 and the image and planning data developed in the pathway planning phase, described above.

Memory 502 may include any non-transitory computer-readable storage media for storing data and/or software that is executable by processor 504 and which controls the operation of computing device 80. In an embodiment, memory 502 may include one or more solid-state storage devices such as flash memory chips. Alternatively or in addition to the one or more solid-state storage devices, memory 502 may include one or more mass storage devices connected to the processor 504 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 504. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 508 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with computing device 80, such as, for example, a mouse, keyboard, foot pedal, touch screen, and/or voice interface. Output module 512 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A non-transitory computer-readable storage medium storing instructions which, when executed by a computer, cause the computer to:
   cause presentation of a 3D model of a luminal network;
   cause generation of, by an electromagnetic (EM) field generator of a tracking system, an EM field about a patient's chest;
   receive a detection a location of an EM sensor of the tracking system within the EM field;
   determine a position of a tool within the patient's chest based on the location of the EM sensor detected;
   cause display of an indication of the position of the tool on the 3D model;
   provide guidance for positioning a cone beam computed tomography (CBCT) imaging device based on the location of the EM sensor detected;
   actively track a location of the CBCT imaging device via a sensor included in the CBCT imaging device;
   determine whether the CBCT imaging device is moved into the EM field based at least in part on data received by the tracking system from the sensor included in the CBCT imaging device;
   compensate for distortion of the EM field caused by the CBCT imaging device being disposed within the EM field by adjusting the indication of the position of the tool displayed on the 3D model in response to determining that the CBCT imaging device is moved into the EM field;
   cause the EM field generator to be disabled after providing guidance for positioning the CBCT imaging device based on the location of the EM sensor detected in response to determining that the CBCT imaging device is not moved into the EM field;
   receive CBCT image data of the patient's chest from the CBCT imaging device while the EM field generator is disabled; and
   cause the EM field generator to be enabled after receiving the CBCT image data of the patient's chest while the EM field generator is disabled.

2. The non-transitory computer-readable storage medium according to claim 1, further comprising instructions which, when executed, cause the computer to receive image data of a portion of the patient's chest about the location of the EM sensor detected to generate the CBCT image data.

3. The non-transitory computer-readable storage medium according to claim 2, wherein the CBCT image data is generated during a first phase of the patient's respiratory cycle, and the instructions, when executed, cause the computer to receive the image data of the portion of the patient's chest about the location of the EM sensor detected to generate additional CBCT image data during a second phase of the patient's respiratory cycle.

4. The non-transitory computer-readable storage medium according to claim 3, further comprising instructions which, when executed, cause the computer to:
   monitor the patient's respiratory cycle to determine a current phase of the patient's respiratory cycle; and
   display one of the CBCT image data or the additional CBCT image data corresponding to the current phase of the patient's respiratory cycle.

5. The non-transitory computer-readable storage medium according to claim 4, wherein the monitor of the patient's respiratory cycle is based on data received from one or more reference sensors located on the patient's chest.

6. The non-transitory computer-readable storage medium according to claim 4, wherein the monitor of the patient's respiratory cycle is based on a ventilator connected to the patient.

7. The non-transitory computer-readable storage medium according to claim 3, further comprising instructions which, when executed, cause the computer to:
monitor the patient's respiratory cycle to determine a current phase of the patient's respiratory cycle; and
cause display of a notification when the current phase of the patient's respiratory cycle does not correspond to the CBCT image data or the additional CBCT image data.

8. The non-transitory computer-readable storage medium according to claim 2, further comprising instructions which, when executed, cause the computer to:
identify the tool in the CBCT image data;
orient the CBCT image data based on a position and orientation of the tool in the CBCT image data; and
cause display of the CBCT image data.

9. The non-transitory computer-readable storage medium according to claim 8, wherein the tool is an ablation device and the instructions, when executed, cause the computer to:
identify a radiating portion of the ablation device;
determine a projected ablation zone based on the position and orientation of the ablation device and ablation settings; and
cause display of an indication of the projected ablation zone on the CBCT image data.

10. The non-transitory computer-readable storage medium according to claim 9, further comprising instructions which, when executed, cause the computer to:
determine an estimated ablation zone based on the position and orientation of the ablation device, the ablation settings, and an elapsed time; and
cause display of an indication of the estimated ablation zone on the CBCT image data.

11. The non-transitory computer-readable storage medium according to claim 1, wherein the 3D model includes an indication of a target location and a pathway for navigating the tool to the target location.

12. The non-transitory computer-readable storage medium according to claim 11, wherein a first portion of the pathway to the target location is located inside of the luminal network and a second portion of the pathway to the target location is located outside of the luminal network.

13. The non-transitory computer-readable storage medium according to claim 12, wherein the CBCT image data is received while the tool is navigated along the second portion of the pathway to the target location.

14. The non-transitory computer-readable storage medium according to claim 13, wherein the second portion of the pathway to the target location is updated based on the CBCT image data.

15. The non-transitory computer-readable storage medium according to claim 1, further comprising instructions which, when executed, cause the computer to provide a notification that the position of the CBCT imaging device is causing the distortion of the EM field.

16. The non-transitory computer-readable storage medium according to claim 1, further comprising instructions which, when executed, cause the computer to provide a notification when one or more reference sensors on the patient's chest indicate that the patient has moved during imaging.

17. A non-transitory computer-readable storage medium storing instructions which, when executed by a computer, cause the computer to:
receive a detection of a location of an electromagnetic (EM) sensor within an EM field generated by an EM field generator of a tracking system;
determine a position of a tool within a patient's chest based on the location of the EM sensor detected;
cause display of an indication of the position of the tool on a 3D model;
provide guidance for positioning an imaging device based on the location of the EM sensor detected;
actively track a location of the imaging device via a sensor included in the imaging device;
determine whether the imaging device is moved into the EM field based at least in part on data received by the tracking system from the sensor included in the imaging device;
compensate for distortion of the EM field caused by the imaging device being disposed within the EM field by adjusting the indication of the position of the tool displayed on the 3D model in response to determining that the imaging device is moved into the EM field;
cause the EM field generator to be disabled after providing guidance for positioning the imaging device based on the location of the EM sensor detected in response to determining that the imaging device is not moved into the EM field;
receive image data of the patient's chest from the imaging device while the EM field generator is disabled; and
cause the EM field generator to be enabled after receiving the image data of the patient's chest while the EM field generator is disabled.

18. The non-transitory computer-readable storage medium according to claim 17, further comprising instructions which, when executed, cause the computer to provide a notification when one or more reference sensors on the patient's chest indicate that the patient has moved during imaging.

19. A non-transitory computer-readable storage medium storing instructions which, when executed by a computer, cause the computer to:
determine a position of a tool within a patient's chest based on a location of an electromagnetic (EM) sensor within an EM field generated by an EM field generator of a tracking system;
cause display of an indication of the position of the tool on a 3D model;
actively track a location of an imaging device via a sensor included in the imaging device;
determine whether the imaging device is moved into the EM field based at least in part on data received by the tracking system from the sensor included in the imaging device;
compensate for distortion of the EM field caused by the imaging device being disposed within the EM field by adjusting the indication of the position of the tool displayed on the 3D model in response to determining that the imaging device is moved into the EM field;
cause the EM field generator to be disabled after providing guidance for positioning the imaging device based on the location of the EM sensor detected in response to determining that the imaging device is not moved into the EM field;
receive image data of the patient's chest from the imaging device while the EM field generator is disabled; and cause the EM field generator to be enabled after receiving the image data of the patient's chest while the EM field generator is disabled.

20. The non-transitory computer-readable storage medium according to claim 19, further comprising instructions which, when executed, cause the computer to provide a notification when one or more reference sensors on the patient's chest indicate that the patient has moved during imaging.

* * * * *